United States Patent [19]

Sayigh et al.

[11] 4,029,705

[45] June 14, 1977

[54] PURIFICATION PROCESS FOR MDA

[75] Inventors: Adnan A. R. Sayigh, North Haven; Kwok K. Sun, Hamden; Henri Ulrich, Northford, all of Conn.

[73] Assignee: The Upjohn Company, Kalamazoo, Mich.

[22] Filed: Aug. 18, 1975

[21] Appl. No.: 605,753

[52] U.S. Cl. .......................................... 260/570 D
[51] Int. Cl.$^2$ ....................................... C07C 85/16
[58] Field of Search ............................. 260/570 D

[56] References Cited

UNITED STATES PATENTS

| 3,676,497 | 7/1972 | Recchia | 260/570 |
|---|---|---|---|
| 3,857,890 | 12/1974 | Recchia | 260/570 |
| 3,860,637 | 1/1975 | Bentley | 260/570 |

FOREIGN PATENTS OR APPLICATIONS

| 863,983 | 2/1971 | Canada | 260/570 |
|---|---|---|---|
| 1,127,347 | 9/1968 | United Kingdom | 260/570 |

OTHER PUBLICATIONS

Allied Chemical, "Aniline", p. 35 (1964).

*Primary Examiner*—Robert V. Hines
*Attorney, Agent, or Firm*—Denis A. Firth; John Kekich

[57] ABSTRACT

A process is described for the selective removal of 2,2'- and 2,4'-diaminodiphenylmethanes from mixtures containing 2,2'-, 2,4'- and 4,4'-diaminodiphenylmethanes and polyamines by heating these mixtures in the presence of aqueous hydrochloric acid (55 to 95 percent by equivalents based on the total amine in the starting material) and formaldehyde. The process is particularly useful to facilitate the isolation of substantially pure 4,4'-isomer from aniline-formaldehyde condensation products. The pure 4,4'-isomer is a valuable intermediate for polyamides as well as for the corresponding diisocyanate. The by-products of the reaction are oligomeric polymethylene polyphenyl polyamines which are also useful as curing agents and intermediates for polymethylene polyphenyl polyisocyanates and the like.

8 Claims, No Drawings

PURIFICATION PROCESS FOR MDA

BACKGROUND OF THE INVENTION

1. Field of the Invention

This invention relates to the preparation of diamines and is more particularly concerned with the selective removal of 2,2'- and 2,4'-diaminodiphenylmethanes from mixtures containing 2,2'-, 2,4'- and 4,4'-diaminodiphenylmethanes and, optionally, oligomeric polymethylene polyphenyl polyamines.

2. Description of the Prior Art

The condensation of aniline with formaldehyde in the presence of catalysts such as mineral acids, siliceous materials and the like, is well-known in the art; see, for example, U.S. Pat. Nos. 2,638,730; 2,950,263; 3,260,751; 3,277,173; 3,297,759; 3,362,979; and 3,476,806. The principal component of the product of this condensation is di(aminophenyl)methane the remaining components being oligomeric methylene polyphenyl polyamines, e.g. triamines, tetramines, etc. The proportion of diamine present in the mixture depends to a large extent on the molar proportion of aniline to formaldehyde. In general, the higher the proportion of aniline to formaldehyde, the higher the proportion of diamine in the product. The majority of the diamine is obtained as the 4,4'-isomer, the 2,4'-isomer being present in relatively minor proportion together with very small amounts of the 2,2'-isomer. The proportion of the isomers in any given product is dependent upon the reactant proportions and conditions employed in the reaction.

To date, no process has been devised which will give directly a product containing diamine which is exclusively in the form of the 4,4'-isomer. Proportions of 4,4'-isomer as high as 98 percent and as low as 40 percent or less have been reported. However, for many purposes, particularly where the diamine is to be used as an intermediate in the preparation of linear polyamides, polyimides and similar polymers, it is desirable, if not essential, that the diamine be substantially pure 4,4'-isomer, i.e., that the total content of the 2,2'- and the 2,4'-isomers be only 2 percent by weight or less. Accordingly, the diamine isolated from the aniline-formaldehyde condensation (or the corresponding diisocyanate obtained by phosgenation of the diamine alone or as part of the mixture of polyamines obtained in the condensation) has been purified by conventional techniques such as fractional distillation, fractional crystallization, and the like, to achieve the desired purity of 4,4'-isomer. Not only are such techniques tedious and expensive to operate on a commercial scale, but they produce, as by-product, the 2,2'- and the 2,4'-isomers, or fractions enriched in the 2,2'- and the 2,4'-isomers, which are of much less utility than the 4,4'-isomer. We have now found that the 2,2'- and the 2,4'-diaminodiphenylmethanes can be removed selectively and conveniently to yield substantially pure 4,4'-diaminodiphenylmethane by a process which will be described below. This process can be applied successfully to isomeric mixtures of diaminodiphenylmethanes as well as to mixtures of 4,4'-isomer, 2,2'- and 2,4'-isomers and mixtures of said isomers with oligomeric polyamines.

SUMMARY OF THE INVENTION

This invention comprises a process for selectively removing 2,2'- and 2,4'-diaminodiphenylmethanes from mixtures containing 2,2'-, 2,4'- and 4,4'-diaminodiphenylmethanes by heating said mixture of isomers with formaldehyde in the presence of aqueous hydrochloric acid, at a temperature of 30° C to 100° C, the amount of hydrochloric acid present being in the range of 0.55 to 0.95 equivalents per total amine equivalent.

The 2,2'- and 2,4'-diaminodiphenylmethanes employed in the above process can be in the form of mixtures of 2,2'-, 2,4'- and 4,4'-diaminodiphenylmethanes or in the form of a mixture of 2,2'-, 2,4'- and 4,4'-isomers with oligomeric polyamines such as the mixtures isolated from the reaction product of aniline and formaldehyde under conditions well-known in the art (supra).

DETAILED DESCRIPTION OF THE INVENTION

The process of the invention is carried out conveniently by bringing the reactants together, in any order, and heating the resulting mixtures at a temperature within the range of about 30° C to about 100° C and preferably at about 80° to 100° C until routine analytical procedures, carried out on an aliquot, indicate that the isomerization has proceeded to the required extent. Advantageously, the amines are first dissolved in the aqueous hydrochloric acid solution and the formaldehyde is added thereto. The formaldehyde can be employed in any of the forms commonly available including paraformaldehyde but is preferably employed in the form of the aqueous solution containing approximately 3.7 to 37 percent w/w of formaldehyde which is available commercially.

The aqueous hydrochloric acid employed in the reaction mixture advantageously has an initial concentration within the range of about 0.1 N to about 5.0 N and preferably within the range of about 1.0 N to about 2.0 N. As indicated above, the amount of hydrochloric acid employed in the process of the invention is such that, for each equivalent of diamine, there is employed from 0.55 to 0.95 equivalents of hydrochloric acid. When the mixed diaminodiphenylmethanes, employed as starting material in the process of the invention, are present in admixture with oligomeric methylene polyphenyl polyamines, the amount of hydrochloric acid employed is within the range of 0.55 to 0.95 equivalents per equivalents of total amine.

The proportion of formaldehyde which is employed in the process of the invention varies depending on the proportions of the 2,2'- and 2,4'-isomers in the starting mixture. Advantageously the proportion of formaldehyde is in the range of about 0.2 to about 2.0 moles per mole of the total of 2,2'- and 2,4'-isomers in the starting material and preferably within the range of about 0.5 to about 1.5 moles per mole of the total of the 2,2'- and 2,4'-isomers. When the diamines are present in admixture with oligomeric polyamines, the proportion of the formaldehyde is calculated on the same basis.

The mixture of amines, hydrochloric acid and formaldehyde is heated at a temperature in the above quoted range with stirring until the reaction is completed or has reached any desired stage. The progress of the reaction can be followed by routine analytical techniques performed on aliquots. Such techniques include gas liquid phase and thin layer chromatography and the like. When the reaction has reached the desired stage, the diamine and oligomers are isolated from the reaction mixture by neutralizing the hydrochloric acid remaining in the reaction mixture, using a base such as sodium hydroxide, and extracting the liberated amines using an appropriate organic solvent such as chloroform, methylene chloride, benzene, toluene, chlorobenzene, dichlorobenzene, ethylacetate, and the like. The diamine is purified, if desired, by fractional distillation, fractional crystallization and the like.

The chief by-products produced in the process of the invention are oligomeric methylene polyphenyl polyamines. Such products are themselves useful, illustratively, as curatives for epoxy resins and as intermediates in that they can be phosgenated to form the corresponding polymethylene polyphenyl polyisocyanates. Indeed, in a particular embodiment of the process of the invention the total amine product from the process, i.e., the mixture of 4,4'-diaminodiphenylmethane and oligomeric methylene polyphenyl polyamines, is isolated as such and phosgenated, using conventional procedures, to the corresponding mixture of 4,4'-diisocyanatodiphenylmethane and oligomeric polymethylene polyphenyl polyisocyanates. The mixture is useful as such in the preparation of rigid polyurethane and polyisocyanurate foams and in the preparation of adhesives, rigid non-cellular plastics and the like using techniques well-known in the art. Alternatively, the mixture can be subjected to fractional distillation using thin film evaporators, employing techniques such as those described in U.S. Pat. No. 3,471,543, to isolate substantially pure 4,4'-diisocyanatodiphenylmethane. The latter is useful as an intermediate in the preparation of linear polyurethane elastomers using techniques well-known in the art.

As set forth above, the process of the invention can be applied to selectively remove 2,2'- and 2,4'-diaminodiphenylmethanes from admixtures with 4,4'-diaminodiphenylmethane and/or with oligomeric methylene polyphenyl polyamines. In a particular embodiment the process of the invention is applied to a mixture of 2,2'-, 2,4'- and 4,4'-diaminodiphenylmethanes which mixture has been isolated as the forecut in the fractional distillation of 4,4'-diaminodiphenylmethane containing minor amounts of the 2,2'- and the 2,4'-diaminodiphenylmethanes, the latter having been isolated from the reaction of aniline and formaldehyde using processes commercially employed in the art.

The process of the invention can, therefore, be employed as a means of isolating substantially pure 4,4'-isomer (i.e., containing at least 98 percent by weight of 4,4'-isomer) from its admixture with one or both of the corresponding 2,2'- and 2,4'-isomers. Thus such mixtures are subjected to the process of the invention and the 4,4'-isomer is isolated in substantially pure form from the reaction product by fractional distillation, fractional crystallization and the like.

It is to be noted that, although the process of the invention has been largely in terms of treating admixtures of the 4,4'-isomer with both the 2,2'- and 2,4'-isomers, since such mixtures are the ones most commonly encountered in practice, the process of the invention can be applied equally successfully to the treatment of admixtures of the 4,4'-isomer with either 2,2'- or 2,4'-isomer alone.

The following examples describe the manner and process of making and using the invention and set forth the best mode contemplated by the inventors of carrying out the invention but are not to be construed as limiting.

EXAMPLE 1

A total of 1.4 g. (1.75 mmol.) of 3.7% w/w aqueous formaldehyde was added in one batch to a mixture of 1.0 g. (5.05 mmol.) of diaminodiphenylmethane (containing 15 percent by weight of 2,4'-isomer and 85 percent by weight of 4,4'-isomer) and 8.5 ml. (8.5 mmol.) of N aqueous hydrochloric acid. The mixture was heated with stirring at 95° C for 1 hour at the end of which time gas liquid phase chromatography (glpc) of an aliquot indicated that the proportion of 2,4'-isomer in the diamine had been reduced to 1.1 percent by weight. The reaction mixture was thereupon cooled to room temperature and neutralized by the addition of 5N aqueous sodium hydroxide solution. The liberated amine was extracted with chloroform and the chloroform extract was washed with deionized water, dried over anhydrous sodium sulfate and evaporated to dryness. The residue was a mixture of diaminodiphenylmethane and oligomeric polymethylene polyphenyl polyamines which was found by glpc, using 2,2-di(4-aminophenyl)propane as internal standard, to contain 56 percent by weight of the starting amount of the diaminodiphenylmethanes, the proportion of 2,4'-isomer to 4,4'-isomer present therein being as stated above.

EXAMPLE 2

A total of 2.9 g. (3.62 mmol.) of 3.7% w/w aqueous formaldehyde was added to a mixture of 1.00 g. (5.05 mmol.) of diaminodiphenylmethane (containing equal proportions of 2,4'- and 4,4'-isomer) and 8.5 ml. (8.5 mmol.) of N aqueous hydrochloric acid and the resulting mixture was stirred and heated at 100° C for 1 hr. At the end of this time the reaction mixture was cooled and neutralized with 5N aqueous sodium hydroxide. The amine which separated was extracted with chloroform and the chloroform was washed with water and dried over anhydrous sodium sulfate before being evaporated to dryness. The residue was found by glpc to contain 23 percent by weight of the starting diamines, the remainder being oligomeric polyamines. The diamine contained 99 percent by weight of 4,4'-isomer and only 1 percent by weight of 2,4'-isomer.

EXAMPLE 3

A mixture of 0.84 g. (1.04 mmol.) of 3.7% w/w aqueous formaldehyde, 1 g. (5.05 mmol.) of diaminodiphenylmethane (containing 15 percent by weight of 2,4'-isomer and 85 percent by weight of 4,4'-isomer) and 9 ml. (9 mmol.) of N aqueous hydrochloric acid was heated at 95° C for 1 hour. The resulting product was cooled to room temperature, neutralized with 5N aqueous sodium hydroxide and the liberated amine was extracted with chloroform. The chloroform extract was dried over anhydrous sodium sulfate and evaporated to dryness. The residue was found by glpc to contain 81.5 percent by weight of the starting diamine. The diamine was found to contain 4.0 percent by weight of 2,4'-isomer and 96.0 percent by weight of 4,4'-isomer.

EXAMPLE 4

The procedure of Example 3 was repeated except that the starting mixture of diamines there used was replaced by a mixture containing 88 percent by weight of 4,4'-isomer, 10.5 percent by weight of 2,4'-isomer and 1.5 percent by weight of 2,2'-isomer. The diamine in the product so obtained was found to contain approximately 98 percent of 4,4'-isomer the remainder being 2,4'-isomer there being no detectable amount of 2,2'-isomer.

What is claimed is:

1. A process for selectively removing 2,2'- and 2,4'-diaminodiphenylmethanes from mixtures thereof with 4,4'-diaminodiphenylmethane said mixtures having been previously isolated from the product of condensing aniline with formaldehyde which process comprises heating an aqueous mixture consisting essentially of said diaminodiphenylmethanes, hydrochloric acid, and formaldehyde at a temperature of 30° C to 100° C, the amount of hydrochloric acid present being from 0.55 to 0.95 equivalents per equivalent of diamine present in the reaction mixture.

2. The process of claim 1 wherein the diamine mixture employed as starting material has been obtained by the condensation of aniline and formaldehyde.

3. The process of claim 2 wherein the diamine mixture employed as starting material also includes oligomeric methylene polyphenyl polyamines.

4. The process of claim 1 wherein the formaldehyde is employed in an amount corresponding to from 0.5 mole to 1.5 mole per mole of the total of 2,2'- and 2,4'-diaminodiphenylmethane present in the starting material.

5. The process of claim 1 wherein the diamine mixture employed as starting material is the forecut obtained in the fractional distillation of 4,4'-diaminodiphenylmethane containing minor amounts of 2,2'- and 2,4'-diaminodiphenylmethane.

6. A process for the isolation of substantially pure 4,4'-diaminodiphenylmethane from a mixture of said isomer with a minor amount of at least one of the corresponding 2,2'- and 2,4'-isomers said mixture having been previously isolated from the product of condensing aniline with formaldehyde which process comprises heating said mixture with a mixture consisting essentially of aqueous hydrochloric acid and formaldehyde at a temperature of 30° C to 100° C to obtain a mixture of 4,4'-diaminodiphenylmethane and oligomeric methylene polyphenyl polyamines substantially free from 2,2'- and 2,4'-diaminodiphenylmethane, and recovering said 4,4'-diaminodiphenylmethane from said product.

7. The process of claim 6 wherein the formaldehyde is employed in an amount corresponding to from 0.5 mole to 1.5 mole per mole of the total of 2,2'- and 2,4'-diaminodiphenylmethanes in said starting material.

8. The process of claim 6 wherein the amount of hydrochloric acid employed is from about 0.55 to about 0.95 equivalents per equivalent of total amine present in the starting material.

* * * * *